(12) United States Patent
Redding et al.

(10) Patent No.: US 10,073,060 B2
(45) Date of Patent: Sep. 11, 2018

(54) NON-CONTACT ACOUSTIC INSPECTION METHOD FOR ADDITIVE MANUFACTURING PROCESSES

(71) Applicant: General Electric Company, Schenectady, NY (US)

(72) Inventors: MacKenzie Ryan Redding, Cincinnati, OH (US); Scott Alan Gold, Waynesville, OH (US); Thomas Graham Spears, Cincinnati, OH (US)

(73) Assignee: General Electric Company, Schenectady, NY (US)

( * ) Notice: Subject to any disclaimer, the term of this patent is extended or adjusted under 35 U.S.C. 154(b) by 154 days.

(21) Appl. No.: 14/946,451

(22) Filed: Nov. 19, 2015

(65) Prior Publication Data

US 2017/0146489 A1 May 25, 2017

(51) Int. Cl.
*G01N 29/24* (2006.01)
*G01N 29/02* (2006.01)

(52) U.S. Cl.
CPC ......... *G01N 29/02* (2013.01); *G01N 29/2418* (2013.01); *G01N 2291/267* (2013.01)

(58) Field of Classification Search
CPC ............... G01N 29/02; G01N 29/2418; G01N 2291/267
USPC ......................................................... 73/645
See application file for complete search history.

(56) References Cited

U.S. PATENT DOCUMENTS

| | | |
|---|---|---|
| 4,144,766 A | 3/1979 | Wehrmeister |
| 4,419,562 A | 12/1983 | Jon et al. |
| 4,644,127 A | 2/1987 | La Rocca |
| 5,065,630 A | 11/1991 | Hadcock et al. |
| 5,445,027 A | 8/1995 | Zorner |
| 5,487,733 A | 1/1996 | Caizza et al. |
| 5,952,576 A | 9/1999 | Schwarz |
| 6,078,397 A | 6/2000 | Monchalin et al. |
| 6,628,404 B1 | 9/2003 | Kelley et al. |
| 6,732,587 B2 | 5/2004 | Lorraine et al. |

(Continued)

FOREIGN PATENT DOCUMENTS

| | | |
|---|---|---|
| AU | 623417 | 5/1992 |
| GB | 2508335 | 6/2014 |

(Continued)

OTHER PUBLICATIONS

Extended European Search Report and Opinion issued in connection with corresponding EP Application No. 16199369.6 dated Apr. 12, 2017.

(Continued)

*Primary Examiner* — J M Saint Surin
(74) *Attorney, Agent, or Firm* — General Electric Company; Brian Overbeck

(57) ABSTRACT

A method for inspecting an additive manufacturing process in which a directed energy source is used to create a weld pool at an exposed build surface of a mass of powdered material, and selectively fuse the powdered material to form a workpiece. The inspection method includes: using a non-contact method to generate an acoustic wave in the build surface; using a noncontact method to measure displacement of the build surface in response to the acoustic wave; and determining at least one sub-surface material property of the workpiece by analyzing the displacement of the build surface.

17 Claims, 4 Drawing Sheets

(56) References Cited

U.S. PATENT DOCUMENTS

| | | | |
|---|---|---|---|
| 6,925,346 B1 | 8/2005 | Mazumder et al. | |
| 6,940,037 B1 | 9/2005 | Kovacevic et al. | |
| 7,010,982 B2 | 3/2006 | Bergman | |
| 7,057,176 B2 | 6/2006 | Rothenfusser et al. | |
| 7,262,861 B1* | 8/2007 | Pepper | G01B 11/06 |
| | | | 356/502 |
| 8,181,523 B2 | 5/2012 | Batzinger et al. | |
| 8,210,045 B2 | 7/2012 | Caron | |
| 8,303,886 B2 | 11/2012 | Philippi | |
| 8,497,986 B2 | 7/2013 | Ochiai et al. | |
| 8,778,255 B2 | 7/2014 | Banberg et al. | |
| 8,784,721 B2* | 7/2014 | Philippi | B33Y 10/00 |
| | | | 219/121.83 |
| 9,052,273 B2 | 6/2015 | Michaut | |
| 9,056,368 B2 | 6/2015 | Stork Genannt Wersborg | |
| 9,114,478 B2* | 8/2015 | Scott | B23K 26/703 |
| 9,272,446 B2* | 3/2016 | Grebe | B22F 3/1055 |
| 9,370,789 B2* | 6/2016 | Clemen | B05B 9/002 |
| 9,592,573 B2* | 3/2017 | Daum | B23K 26/342 |
| 9,724,876 B2 | 8/2017 | Cheverton | B29C 64/386 |
| 2003/0154791 A1* | 8/2003 | Wagner | G01N 29/043 |
| | | | 73/596 |
| 2007/0176312 A1 | 8/2007 | Clark et al. | |
| 2007/0234809 A1 | 10/2007 | Klein et al. | |
| 2009/0206065 A1* | 8/2009 | Kruth | B22F 3/1055 |
| | | | 219/121.66 |
| 2014/0060188 A1 | 3/2014 | Singh et al. | |
| 2014/0144895 A1 | 5/2014 | Stork Genannt Wersborg et al. | |
| 2014/0356078 A1 | 12/2014 | Stanowski et al. | |
| 2015/0064047 A1 | 3/2015 | Hyde et al. | |
| 2015/0104802 A1 | 4/2015 | Reep et al. | |
| 2015/0177158 A1 | 6/2015 | Cheverton | |
| 2016/0054205 A1* | 2/2016 | O'Neill | G01N 1/286 |
| | | | 73/863 |
| 2017/0234837 A1* | 8/2017 | Hall | G01N 29/2431 |
| | | | 73/602 |

FOREIGN PATENT DOCUMENTS

| | | |
|---|---|---|
| JP | 2012-163406 A | 8/2012 |
| JP | 2016-060063 A | 4/2016 |
| WO | 2015/109096 A1 | 7/2015 |
| WO | 2016/198885 A1 | 12/2016 |

OTHER PUBLICATIONS

Machine Translation and Notification of Reasons for Refusal issued in connection with corresponding JP Application No. 2016-218495 dated Oct. 24, 2017.

\* cited by examiner

NON-CONTACT ACOUSTIC INSPECTION METHOD FOR ADDITIVE MANUFACTURING PROCESSES

BACKGROUND OF THE INVENTION

This invention relates generally to additive manufacturing, and more particularly to apparatus and methods for inspection and process control in additive manufacturing.

Additive manufacturing is a process in which material is built up layer-by-layer to form a component. Unlike casting processes, additive manufacturing is limited only by the position resolution of the machine and not limited by requirements for providing draft angles, avoiding overhangs, etc. as required by casting. Additive manufacturing is also referred to by terms such as "layered manufacturing," "reverse machining," "direct metal laser melting" (DMLM), and "3-D printing." Such terms are treated as synonyms for purposes of the present invention.

Prior art additive manufacturing processes typically require a post-build inspection process such as computerized tomography ("CT") to verify the integrity of the build. While effective, this process requires undesirable extra time and cost.

Accordingly, there is a need for a real-time inspection process for additive manufacturing.

BRIEF DESCRIPTION OF THE INVENTION

This need is addressed by a method of non-contact acoustic in-situ inspection.

According to one aspect of the technology described herein, a method is provided for inspecting an additive manufacturing process in which a directed energy source is used to create a weld pool at an exposed build surface of a mass of powdered material, and selectively fuse the powdered material to form a workpiece. The method includes: using a noncontact method to generate an acoustic wave in the build surface; using a noncontact method to measure displacement of the build surface in response to the acoustic wave; and determining at least one sub-surface material property of the workpiece by analyzing the displacement of the build surface.

According to another aspect of the technology described herein, a method of making a workpiece includes: depositing a powdered material so as to define a build surface; directing a build beam from a directed energy source to create a weld pool in the build surface, and selectively fuse the powdered material in a pattern corresponding to a cross-sectional layer of the workpiece; using a noncontact method to generate an acoustic wave in the build surface; using a noncontact method to measure displacement of the build surface in response to the acoustic wave; and determining at least one sub-surface material property of the workpiece by analyzing the displacement of the build surface.

According to another aspect of the technology described herein, an apparatus is provided for inspecting an additive manufacturing process in which a directed energy source is used to create a weld pool at an exposed build surface of a mass of powdered material, and selectively fuse the powdered material to form a workpiece. The apparatus includes: a noncontact device configured to generate an acoustic wave in the build surface; and a noncontact device configured to measure displacement of the build surface in response to the acoustic wave.

BRIEF DESCRIPTION OF THE DRAWINGS

The invention may be best understood by reference to the following description taken in conjunction with the accompanying drawing figures in which.

DETAILED DESCRIPTION OF THE INVENTION

Figure 1:
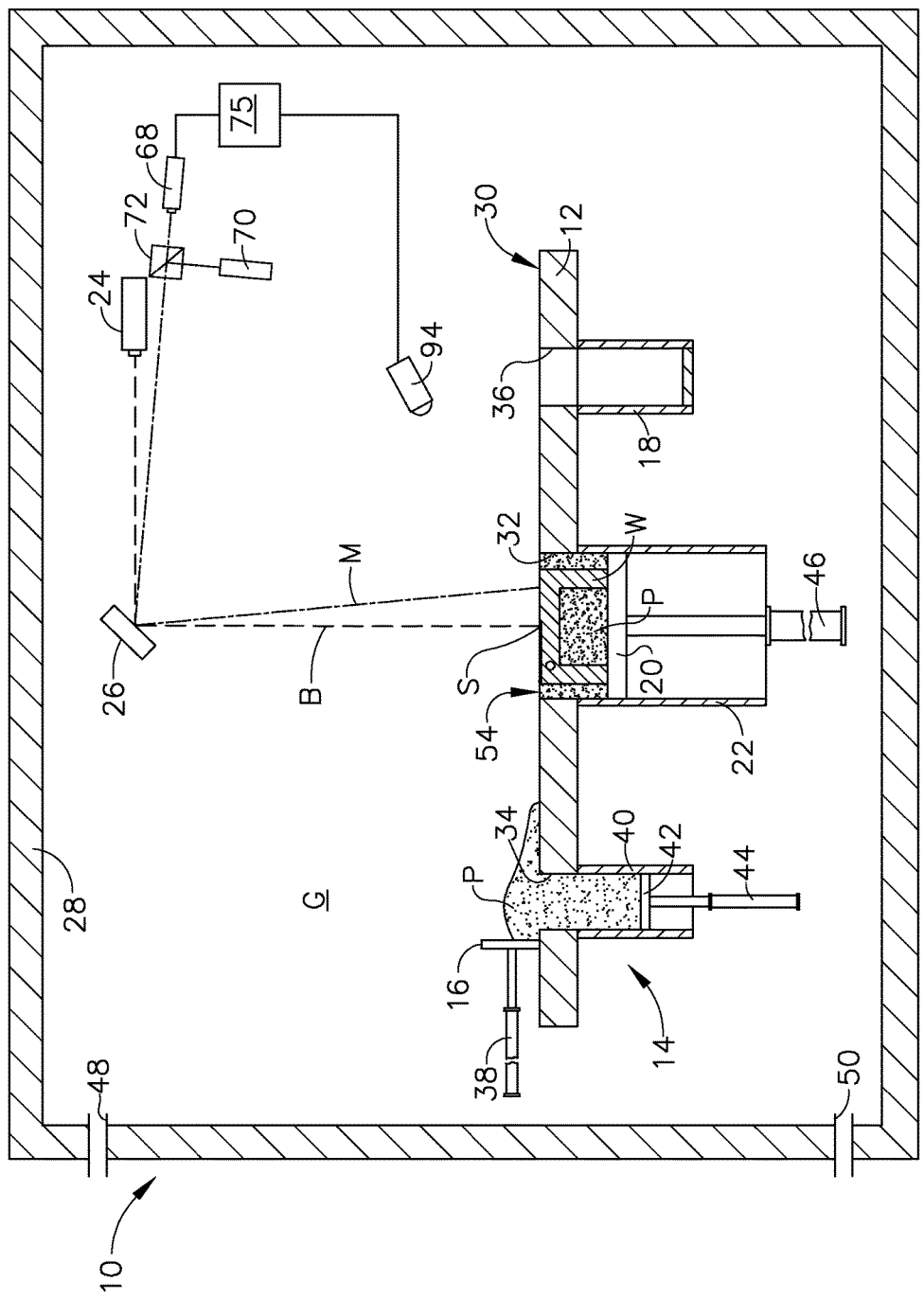
FIG. 1 is a schematic cross-sectional view of an exemplary additive manufacturing apparatus.

Referring to the drawings wherein identical reference numerals denote the same elements throughout the various views, FIG. 1 illustrates schematically an apparatus 10 for carrying out an additive manufacturing method. The basic components are a table 12, a powder supply 14, a scraper or recoater 16, an overflow container 18, a build platform 20 surrounded by a build chamber 22, a directed energy source 24, and a beam steering apparatus 26, all surrounded by an enclosure 28. Each of these components will be described in more detail below.

The table 12 is a rigid structure defining a planar worksurface 30. The worksurface 30 is coplanar with and defines a virtual workplane. In the illustrated example, it includes a build opening 32 communicating with the build chamber 22 and exposing the build platform 20, a supply opening 34 communicating with the powder supply 14, and an overflow opening 36 communicating with the overflow container 18.

The recoater 16 is a rigid, laterally-elongated structure that lies on the worksurface 30. It is connected to an actuator 38 operable to selectively move the recoater 16 along the worksurface 30. The actuator 38 is depicted schematically in FIG. 1, with the understanding devices such as pneumatic or hydraulic cylinders, ballscrew or linear electric actuators, and so forth, may be used for this purpose.

The powder supply 14 comprises a supply container 40 underlying and communicating with the supply opening 34, and an elevator 42. The elevator 42 is a plate-like structure that is vertically slidable within the supply container 40. It is connected to an actuator 44 operable to selectively move the elevator 42 up or down. The actuator 44 is depicted schematically in FIG. 1, with the understanding that devices such as pneumatic or hydraulic cylinders, ballscrew or linear electric actuators, and so forth, may be used for this purpose. When the elevator 42 is lowered, a supply of powder "P" of a desired composition (for example, metallic, ceramic, and/or organic powder) may be loaded into the supply container 40. When the elevator 42 is raised, it exposes the powder P above the worksurface 30.

The build platform 20 is a plate-like structure that is vertically slidable below the build opening 32. It is connected to an actuator 46 operable to selectively move the build platform 20 up or down. The actuator 46 is depicted schematically in FIG. 1, with the understanding that devices such as pneumatic or hydraulic cylinders, ballscrew or linear electric actuators, and so forth, may be used for this purpose. When the build platform 20 is lowered into the build chamber 22 during a build process, the build chamber 22 and the build platform 20 collectively surround and support a mass of powder P along with any components being built.

This mass of powder is generally referred to as a "powder bed", and this specific category of additive manufacturing process may be referred to as a "powder bed process".

The overflow container 18 underlies and communicates with the overflow opening 36, and serves as a repository for excess powder P.

The directed energy source 24 may comprise any known device operable to generate a beam of suitable power and other operating characteristics to melt and fuse the metallic powder during the build process, described in more detail below. For example, the directed energy source 24 may be a laser. Other directed-energy sources such as electron beam guns are suitable alternatives to a laser.

The beam steering apparatus 26 may include one or more mirrors, prisms, magnetic fields, and/or lenses and provided with suitable actuators, and arranged so that a beam "B" from the directed energy source 24 can be focused to a desired spot size and steered to a desired position in plane coincident with the worksurface 30. For purposes of convenient description, this plane may be referred to as an X-Y plane, and a direction perpendicular to the X-Y plane is denoted as a Z-direction (X, Y, and Z being three mutually perpendicular directions). The beam B may be referred to herein as a "build beam".

The enclosure 28 serves to isolate and protect the other components of the apparatus 10. It may be provided with a flow of an appropriate shielding gas "G", for example nitrogen, argon, or other gases or gas mixtures. The gas G may be provided as a static pressurized volume or as a dynamic flow. The enclosure 28 may be provided with inlet and outlet ports 48, 50 respectively for this purpose.

The basic build process for a workpiece W using the apparatus described above is as follows. The build platform 20 is moved to an initial high position. The build platform 20 is lowered below the worksurface 30 by a selected layer increment. The layer increment affects the speed of the additive manufacturing process and the resolution of the workpiece W. As an example, the layer increment may be about 10 to 50 micrometers (0.0003 to 0.002 in.). Powder "P" is then deposited over the build platform 20 for example, the elevator 42 of the supply container 40 may be raised to push powder through the supply opening 34, exposing it above the worksurface 30. The recoater 16 is moved across the worksurface to spread the raised powder P horizontally over the build platform 20. Any excess powder P drops through the overflow opening 36 into the overflow container 18 as the recoater 16 passes from left to right. Subsequently, the recoater 16 may be moved back to a starting position. The leveled powder P may be referred to as a "build layer" 52 and the exposed upper surface thereof may be referred to as a "build surface" 54 (see FIG. 2).

The directed energy source 24 is used to melt a two-dimensional cross-section or layer of the workpiece W being built. The directed energy source 24 emits a beam "B" and the beam steering apparatus 26 is used to steer the focal spot "S" of the build beam B over the exposed powder surface in an appropriate pattern. A small portion of exposed layer of the powder P surrounding the focal spot S, referred to herein as a "weld pool" 56 (best seen in FIG. 2) is heated by the build beam B to a temperature allowing it to sinter, melt, and/or flow, and consequently consolidate. As an example, the weld pool 56 may be on the order of 100 micrometers (0.004 in.) wide. This step may be referred to as fusing the powder P.

The build platform 20 is moved vertically downward by the layer increment, and another layer of powder P is applied in a similar thickness. The directed energy source 24 again emits a build beam B and the beam steering apparatus 26 is used to steer the focal spot S of the build beam B over the exposed powder surface in an appropriate pattern. The exposed layer of the powder P is heated by the build beam B to a temperature allowing it to melt, flow, and consolidate both within the top layer and with the lower, previously-solidified layer.

This cycle of moving the build platform 20, applying powder P, and then directed energy melting the powder P is repeated until the entire workpiece W is complete.

Figure 2:
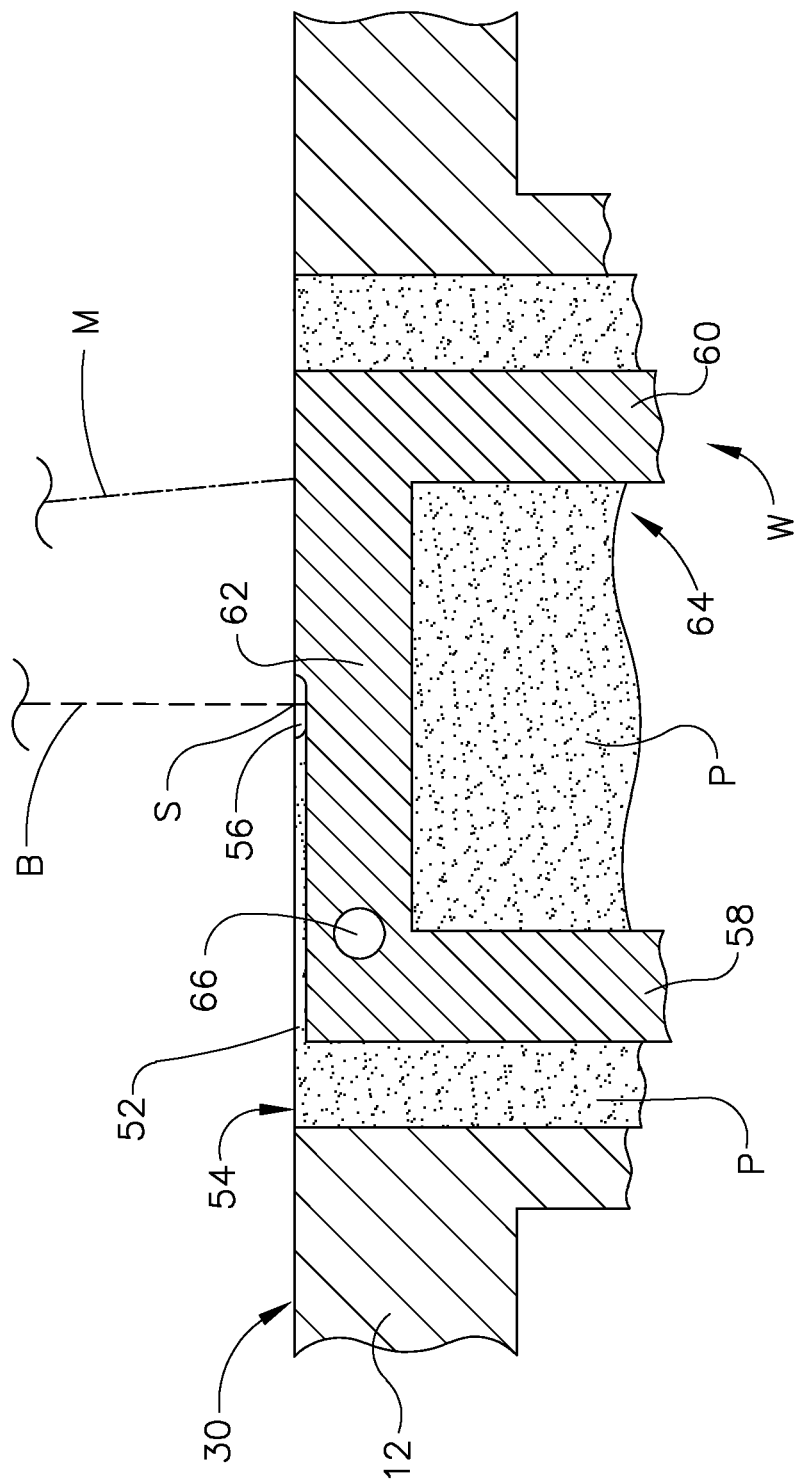
FIG. 2 is an enlarged view of a portion of FIG. 1.

FIG. 2 shows in more detail a workpiece W being constructed in a powder bed of the type described above. The exemplary workpiece W includes a pair of spaced-apart vertical walls 58, 60 interconnected by horizontal wall 62. A cavity 64 is present between the vertical walls 58, 60 and is filled with powder P; additional powder P is present between the vertical walls 58, 60 and the side walls of the build chamber 22. The workpiece W is shown as having an exemplary defect 66 (specifically, a void) disposed therein. Nonlimiting examples of types of defects that can be detected using this method include pores, cracks, and density variations. This particular defect 66 is located below the build surface 54 and thus would not be detectable by a surface inspection method.

A noncontact acoustic inspection process may be incorporated into the build process described above. Generally stated, the inspection process includes using a noncontact method to generate an acoustic wave in the build surface 54, and using a noncontact method to monitor the return signal. In general, this type of inspection process may be referred to as "laser ultrasonic inspection".

Any noncontact means of generating an acoustic wave in the build layer 52 may be used. For example, the action of the build beam B in generating the weld pool 56 inherently generates an acoustic wave radiating out from the weld pool 56. The return signal from this acoustic wave may be monitored.

Means are provided for monitoring the return signal. In the example shown in FIGS. 1 and 2, a low-power continuous-wave ("CW") or pulsed monitoring laser 68, or other suitable device, is positioned so as to be able to direct a monitoring beam M at the build surface 54. The monitoring beam M may be directed through the same beam steering apparatus 26 as the build beam B. Deflection of the build surface 54 (caused by the arrival of the return signal at the build surface 54) in turn cause changes in the index of refraction of the gas "G" above the build surface 54, which ultimately affect the path of the monitoring beam M. The variations in the monitoring beam's path can be sensed by a photodetector 70. This type of acoustic detection is commonly referred to as gas-coupled laser acoustic detection or "GCLAD". Numerous other types of interferometers are known and could be substituted for the monitoring laser 68 and photodetector 70. In this example, the return signal of the monitoring beam M is directed to the photodetector 70 through a beam splitter 72; the specific hardware used to focus and/or direct the monitoring beam M is not critical to the present invention.

Alternatively, the build beam B could be modulated to a reduced power level relative to that used to fuse the powder P, and directed to the build surface 54 to generate an acoustic wave. For example, the power level of the build beam B could be alternated between high and low levels during the building of a layer. Alternatively, a complete layer of powder P could be fused, and then the build beam B could be rescanned over the build surface 54 at a reduced power level to generate an acoustic wave, before applying the next layer increment of powder P.

Figure 3:
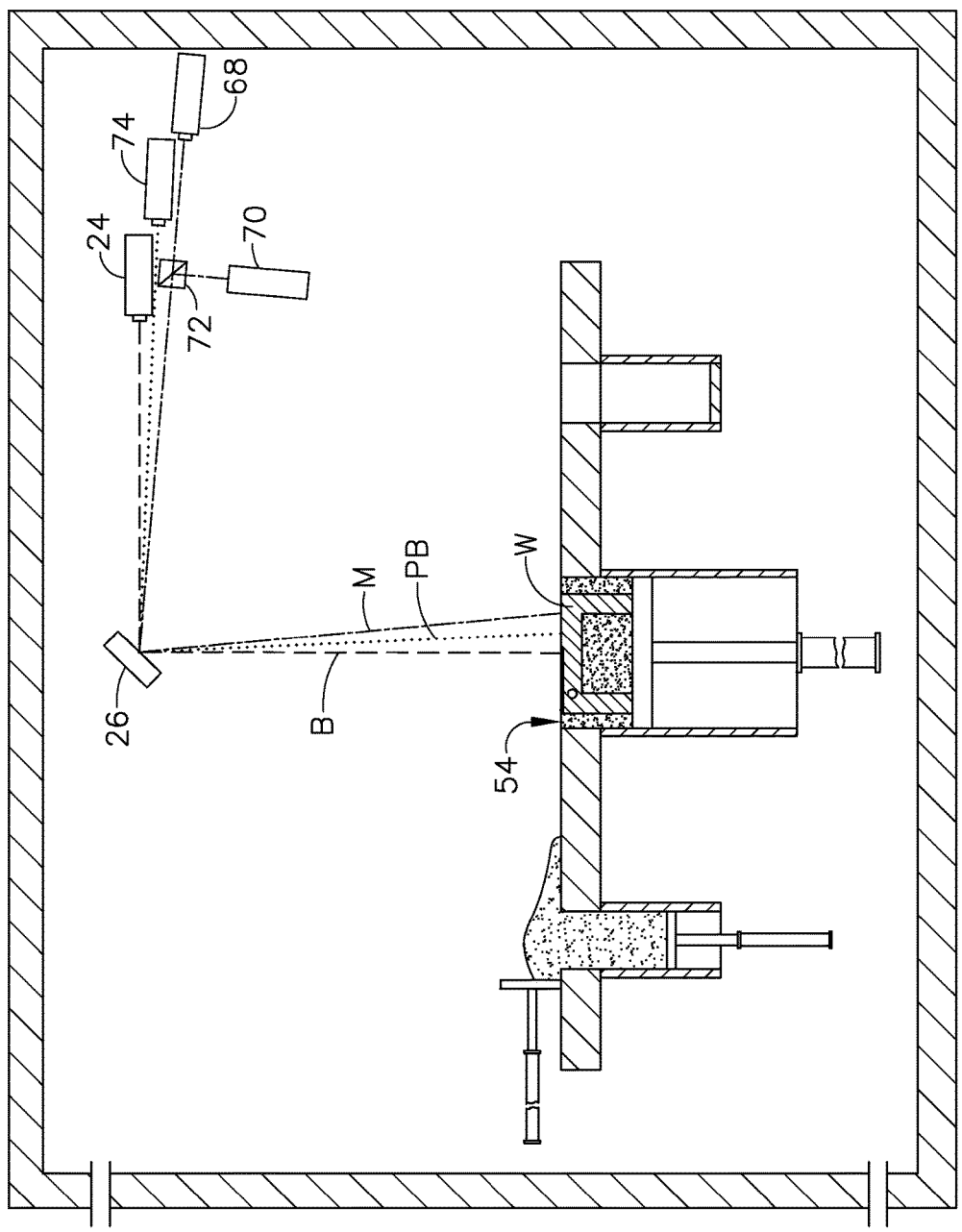
FIG. 3 is a schematic cross-sectional view of an alternative additive manufacturing apparatus.
Figure 4:
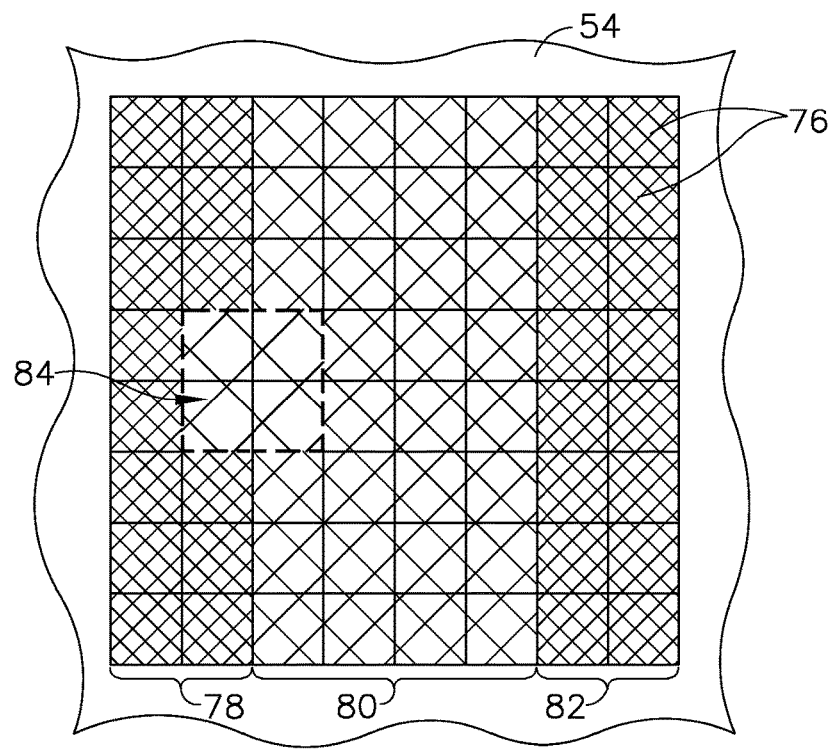
FIG. 4 is a schematic graph showing a matrix of cells representing inspection data.

Alternatively, as shown in FIG. 3, a probe beam PB (generated by a separate probe laser 74 or other suitable radiant energy device) may be used specifically for that purpose. As shown in FIG. 4, the probe beam PB may optionally be directed through the same beam steering apparatus 26 as the build beam B.

The operation of the apparatus 10 including the inspection devices (e.g. probe laser 74, monitoring laser 68, and/or photodetector 70) may be controlled by software running on one or more processors embodied in one or more computers, represented generically in FIG. 1 by controller 75. The same controller 75 may be used to retrieve and analyze sensor data, for statistical analysis, statistical process control, and for feedback control.

The method described above generates information about the round-trip time of an acoustic wave from the build surface 54 to a sub-surface structure and back, which, knowing the speed of sound of the material in question, can be used to determine one or more sub-surface material properties, such as the thickness and/or density of material underlying the build surface 54.

During the inspection process, the surface location where the acoustic wave is induced (e.g. the probe beam focal spot) determines the X-Y location of the thickness/or density measurement on the build surface 54. The focal spot position of the monitoring beam M is not critical; stated another way, the acoustic wave travel path does not have to be directly normal to the build surface 54. Where the monitoring beam focal spot is spaced-away from the focal spot of the probe beam PB (or other source), appropriate computations can be used to determine the actual thickness based on the acoustic return data. For example, measurements may be taken on a plate of known composition and thickness with different relative positions of the probe beam PB and monitoring beam M.

The probe beam PB can be scanned over the build surface 54 in an X-Y or raster pattern to build up information about the workpiece W. For example, FIG. 4 shows a small portion of the build surface 54 represented as a grid of cells 76. Each cell 76 is filled with a hatch pattern representative of the measured material thickness, where a denser hatch pattern indicates greater material thickness. There is a first group 78 of cells corresponding to one of the vertical walls 58, a second group 80 of cells corresponding to the horizontal wall 62, and a third group 82 of cells corresponding to the second vertical wall 60. A fourth group 84 of cells corresponds to the location of the defect 66.

The hatch pattern seen in FIG. 4 is merely for purposes of description. In use, any type of convenient representation may be used to present the thickness data, such as varied patterns, colors, or brightness levels. The data could also be represented by numerical or textual data. Furthermore, the size, type, and arrangement of cells 76 may vary to suit a particular application.

This inspection method generates information about the thickness of material underlying the surface. Distinct changes in material thickness can be an indication of the presence of a defect 66. However, the component may also include discrete thickness changes. In the example workpiece W, there is a discrete thickness change at the transition between the vertical walls 58, 60 and the horizontal wall 62. Depending on the geometry of the workpiece W and the defects, the inspection method may not be able to distinguish such intentional features from defects.

Figure 5:
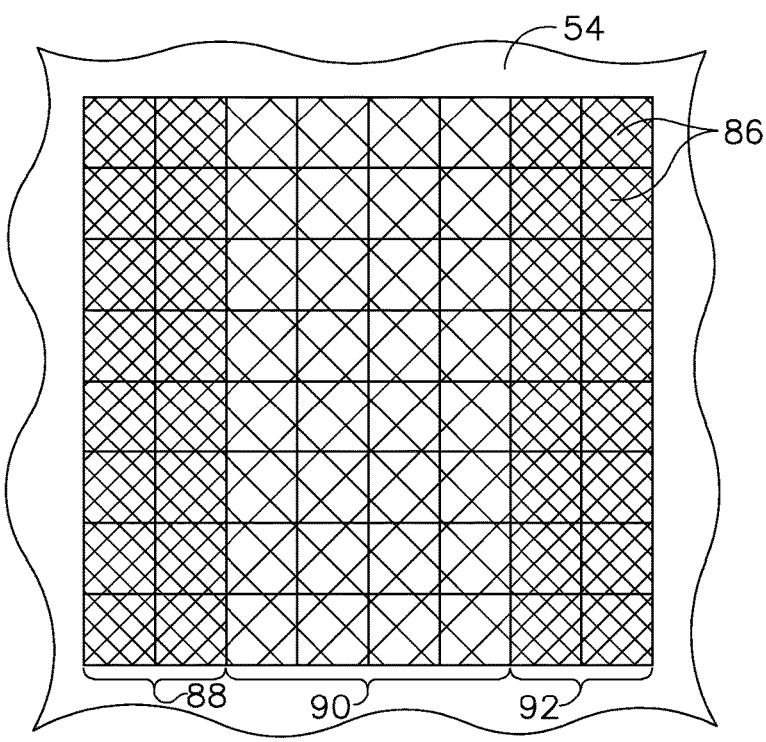
FIG. 5. is a schematic graph showing a matrix of cells representing a model of a workpiece.

Therefore, for best results, the real-time measured data may be compared with a model of a known-good component. For example, the model could include information about the expected material thickness for each X-Y location within each layer. FIG. 5 illustrates a small portion of the build surface 54 represented as a grid of cells 86. Each cell 86 is filled with a hatch pattern representative of the measured material thickness, where a denser hatch pattern indicates greater material thickness. There is a first group 88 of cells corresponding to one of the vertical walls 58, a second group 90 of cells corresponding to the horizontal wall 62 and a third group 92 of cells corresponding to the second vertical wall 60. Comparison of FIG. 5 with FIG. 4 clearly shows that the fourth group 84 of cells 76 shown in FIG. 4 is unexpected and most likely a defect.

The inspection method described above may be implemented for various purposes in an additive manufacturing process. For example, an inspection could be made during the fusing of each build layer 52, or immediately after each build layer 52 is complete, or after several build layers 52 have been completed. This allows confirmation that each layer or group of layers has been built correctly and is free of defects.

If a workpiece is discovered to have a defect, the build process could be abandoned. Alternatively, if a defect is discovered, the apparatus 10 could be used to repair the defect, by directing the build beam B to the workpiece W over the defect, creating a weld pool which remelts the material and permits it to flow into and fill the defect.

The inspection process described above may be used to provide real-time feedback which can be used to modify the additive build process. For example, if the inspection process determines that the build is creating defects, one or more process parameters such as laser power, scanning speed, gas flow, etc. may be changed to restore performance to nominal or eliminate the source of defects.

The inspection process described above may also be used as part of a plan of statistical process control. In particular, the inspection process could be used to identify sources of variation in the process. Process parameters could then be altered in subsequent builds to reduce or eliminate sources of variation.

The data from the acoustic inspection apparatus may be used in conjunction with one or more other process sensors such as photodiodes, pyrometers, acoustic sensors, cameras, or spectrometers. The information from the process sensor may be used as an additional data source for statistical process control or feedback control of the process, as described above. A generic sensor 94 is shown schematically in FIG. 1.

The process described herein has several advantages over the prior art. In particular, it allows mapping the thickness of overhanging layers in an additive structure, and detection of variations from nominal with high precision. This has the potential to eliminate post-build quality control processes such as CT scanning currently used in the prior art.

The foregoing has described an apparatus and method for non-contact acoustic inspection of an additive manufacturing process. All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends any novel one, or any novel combination, of the features disclosed in this specification (including any accompanying potential points of novelty, abstract and drawings), or to any novel one, or any novel combination, of the steps of any method or process so disclosed.

What is claimed is:

1. A method of inspecting an additive manufacturing process in which a directed energy source is used to create a weld pool at an exposed build surface of a mass of powdered material, and to selectively fuse the powdered material to form a workpiece, the method comprising:
   using the directed energy source to generate an acoustic wave in the build surface by modulating the directed energy source to a lower power level compared to a power level used to create the weld pool;
   using a noncontact method to measure displacement of the build surface in response to the acoustic wave; and
   determining at least one sub-surface material property of the workpiece by analyzing the displacement of the build surface.

2. The method of claim 1 wherein the acoustic wave is generated and displacement is measured subsequent to the completion of one or more layers during the additive manufacturing process.

3. The method of claim 1 wherein the surface displacements are measured using a monitoring laser separate from the directed energy source.

4. The method of claim 1 wherein:
   a single beam steering apparatus is used to steer a build beam from the directed energy source and a monitoring beam from a monitoring laser.

5. The method of claim 1 wherein the sub-surface property comprises at least one defect in the workpiece.

6. The method of claim 1 further comprising controlling at least one build process parameter in response to the determined sub-surface property of the workpiece.

7. The method of claim 1 further comprising:
   identifying a defect of the workpiece by analyzing the displacement of the build surface; and
   repairing the defect by using the directed energy source to create a weld pool over the defect, permitting previously-fused material to flow into and fill the defect.

8. The method of claim 1 further comprising controlling at least one build process parameter in response to the determined sub-surface property of the workpiece, in combination with data from at least one other process sensor.

9. The method of claim 1 further comprising comparing the at least one sub-surface material property to a model representative of a known good workpiece.

10. The method of claim 1 wherein the acoustic wave is generated and displacement is measured during the building of a layer in the additive manufacturing process, by alternating between the lower power level used to generate the acoustic wave and a higher power level used to create the weld pool.

11. A method of making a workpiece, comprising:
   depositing a powdered material so as to define a build surface;
   directing a build beam from a directed energy source to create a weld pool in the build surface, and selectively fuse the powdered material in a pattern corresponding to a cross-sectional layer of the workpiece;
   using the directed energy source to generate an acoustic wave in the build surface by modulating the directed energy source to a lower power level compared to a power level used to create the weld pool;
   using a noncontact method to measure displacement of the build surface in response to the acoustic wave; and
   determining at least one sub-surface material property of the workpiece by analyzing the displacement of the build surface.

12. The method of claim 11 further comprising repeating in a cycle the steps of depositing and fusing to build up the workpiece in a layer-by-layer fashion.

13. The method of claim 11 where the acoustic wave is generated and displacement is measured subsequent to the completion of one or more layers during the additive manufacturing process.

14. The method of claim 11 where the surface displacement is measured using a monitoring laser separate from the directed energy source.

15. The method of claim 11 wherein:
   a single beam steering apparatus is used to steer the build beam from the directed energy source and a monitoring beam from a monitoring laser.

16. The method of claim 11 further comprising comparing the at least one sub-surface material property to a model representative of a known good workpiece.

17. The method of claim 11 wherein the acoustic wave is generated and displacement is measured during the building of a layer in the additive manufacturing process, by alternating between the lower power level used to generate the acoustic wave and a higher power level used to create the weld pool.

* * * * *